(12) United States Patent
Ueti et al.

(10) Patent No.: US 10,888,071 B2
(45) Date of Patent: Jan. 12, 2021

(54) IN VITRO PARASITE FEEDING SYSTEM

(71) Applicant: The United States of America, as represented by the Secretary of Agriculture, Washington, DC (US)

(72) Inventors: Massaro W. Ueti, Pullman, WA (US); Glen A. Scoles, Moscow, ID (US); Donald P. Knowles, Jr., Pullman, WA (US)

(73) Assignee: The United States of America, as Represented by The Secretary of Agriculture, Washington, DC (US)

( * ) Notice: Subject to any disclaimer, the term of this patent is extended or adjusted under 35 U.S.C. 154(b) by 813 days.

(21) Appl. No.: 15/050,679

(22) Filed: Feb. 23, 2016

(65) Prior Publication Data
US 2017/0238513 A1 Aug. 24, 2017

(51) Int. Cl.
*A01K 67/02* (2006.01)
*A01K 67/033* (2006.01)

(52) U.S. Cl.
CPC ............ *A01K 67/02* (2013.01); *A01K 67/033* (2013.01)

(58) Field of Classification Search
CPC .......... A01M 1/023; A01M 1/02; A01M 1/10; A01M 1/2005; A01M 1/245; A01M 2200/011; A01M 29/28; A01K 67/02; A01K 67/00
USPC .......................................... 43/107, 123, 121
See application file for complete search history.

(56) References Cited

U.S. PATENT DOCUMENTS

| | | | |
|---|---|---|---|
| 4,307,191 A * | 12/1981 | Ristic .................. | A61K 39/018 435/258.2 |
| 4,850,305 A * | 7/1989 | Georgi ................ | A01K 67/033 119/303 |
| 2009/0313883 A1* | 12/2009 | Olson .................. | A01M 1/023 43/131 |
| 2012/0145081 A1* | 6/2012 | Acar .................... | A01K 67/033 119/6.5 |
| 2014/0283437 A1* | 9/2014 | Brannon ............... | A01M 1/20 43/132.1 |

FOREIGN PATENT DOCUMENTS

CN 102812927 B * 7/2014

* cited by examiner

*Primary Examiner* — Peter M Poon
*Assistant Examiner* — Jeffrey R Larsen
(74) *Attorney, Agent, or Firm* — John D. Fado; Robert D. Jones

(57) ABSTRACT

The system includes a feeding vessel having an inlet, an outlet, and a membrane positioned across an opening in the vessel. Parasites (preferably ticks) are allowed to attach themselves to the membrane so that as a feeding fluid (preferably blood) is circulated through the vessel, the parasites feed on the feeding fluid through the membrane.

19 Claims, 2 Drawing Sheets

IN VITRO PARASITE FEEDING SYSTEM

FIELD OF THE INVENTION

The disclosed method and apparatus relates to an in vitro system for gathering pathogens for research, the production of vaccines, and the production of other products related to diseases spread by parasites. Specifically, the method and apparatus described herein relates to a fluid (preferably blood) circulating system that allows operators to continuously harvest the pathogens and other products produced by ticks throughout the tick life cycle. The harvested products may be used in the production of vaccines and other products used to treat tick-borne illnesses.

BACKGROUND OF THE INVENTION

Ticks are obligate hematophagous ectoparasitic arthropods that cause economic losses to the livestock industry both directly and through transmission of tick-borne pathogens. It is estimated that ticks and tick-borne diseases cause annual losses of more than $20 billion US dollars worldwide. Arthropods, and the disease agents they harbor, are constraining actors for improving and sustaining meat and milk production. Prevention of arthropod-borne diseases is key to the future provision of adequate food supplies.

Prior artificial tick feeding systems tend to mirror mosquito feeding systems—which generally comprise a conventional bowl filled with blood and a membrane stretched across the mouth of the bowl. These feeding systems can be successfully used with mosquitos because mosquitos feed quickly, extract relatively small quantities of blood, and then detach from the host. However, ticks feed more slowly and ingest greater quantities of fluid. A stagnate bowl of blood quickly cools and the blood begins to spoil. Ticks will not remain attached to a bowl of cold spoiling blood. Currently, there is no commercial in vitro tick life cycle feeding system available for production of live pathogen-stage specific vaccines, or for the testing of anti-tick compounds.

A need exists for a long-term in vitro tick feeding system that can simulate the body of a tick's host. The system described herein comprises a relatively simple, flexible, and economical tick feeding system that can be used to closely simulate (at least) a tick's preferred host throughout the entire tick life cycle.

The ability to simulate a full tick life cycle (in vitro) opens up multiple possibilities for researchers and manufacturers of biological products. Among other things, the apparatus disclosed herein comprises a system that is capable of standardized, quality-controlled and economical pathogen harvesting for (among other things) vaccine production. The system may also be used for testing of novel tick control strategies. The in vitro system is designed to provide a continuous flow of blood to feeding ticks, so that the ticks deposit biological materials into a defined medium, which can then be filtered or otherwise processed.

In addition to animal health applications, the system described herein will aid in vaccine development and the study of tick-borne diseases of human medical importance. Such diseases include Lyme disease, human anaplasmosis and human babesiosis. Further, in addition to ticks, the system can be used to replicate a host for other blood-feeding organisms such as leaches, fleas, parasitic worms, and the like.

SUMMARY OF THE INVENTION

This disclosure is directed to an in vitro parasite feeding system. The system includes a feeding vessel having an inlet, an outlet, and a membrane positioned across an opening in the vessel. Parasites (preferably ticks) are allowed to attach themselves to the membrane so that as a feeding fluid (preferably blood) is circulated through the vessel, the parasites ingest the feeding fluid through the membrane.

DETAILED DESCRIPTION OF PREFERRED EMBODIMENTS

Figure 1:
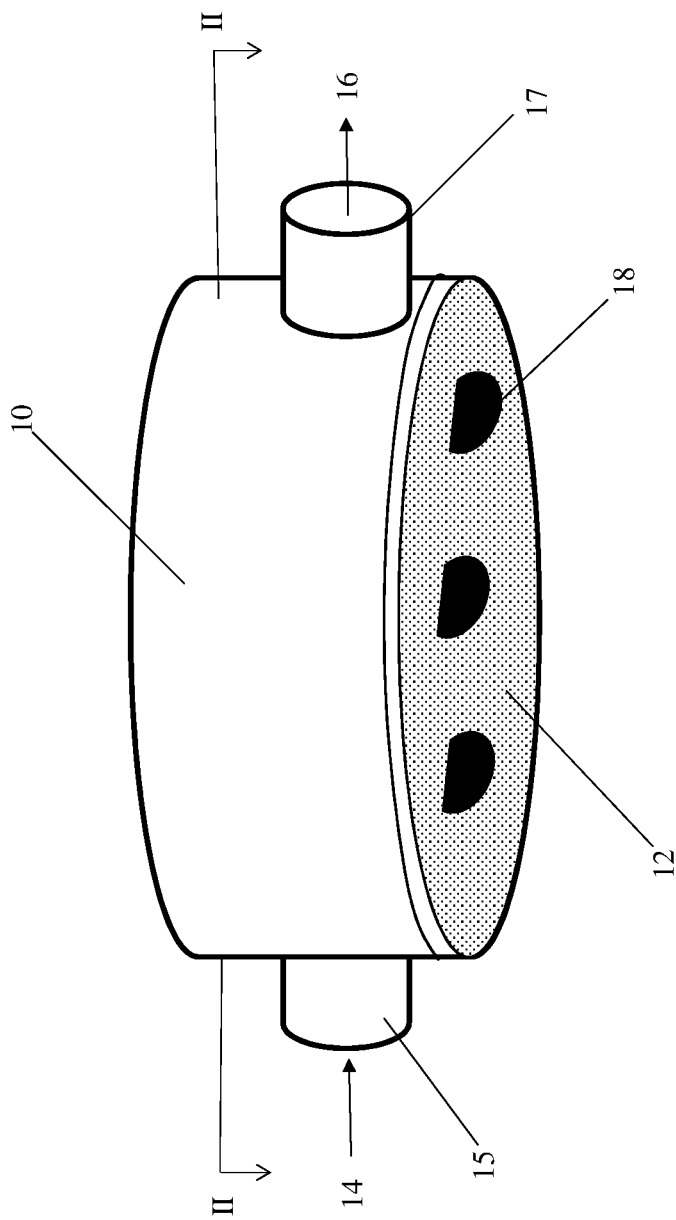
FIG. 1 is a perspective view of a tick feeding vessel shown with ticks in a feeding position.

As generally shown in FIG. 1, the primary components of the system described herein comprises a parasite feeding vessel 10 and a tick attachment membrane 12. In the preferred embodiment, a feeding fluid (preferably animal blood) flows into the parasite feeding vessel 10 in the direction of the arrow 14 through an inlet port 15. After the feeding fluid moves through the body of the vessel 10, the feeding fluid flows out of the vessel 10 in the direction of the arrow 16 through the outlet port 17. As the feeding fluid flows through the feeding vessel 10, at least one parasite 18 is positioned on the membrane 12 and feeds on the feeding fluid through the membrane 12.

For the purposes of this disclosure, a "parasite" is defined as an organism that feeds on the bodily fluid (usually blood) of a living animal host—including a human host. In the preferred embodiment (and throughout this disclosure), the parasite comprises a tick, however in alternative embodiments the parasite may comprise leaches, fleas, parasitic worms, and the like, or any animal that feeds on a live host.

A "feeding fluid" is defined as blood, or other liquid formulations that may nourish or be ingested by parasites. In the preferred embodiment (and throughout this disclosure) the feeding fluid comprises blood. However, in alternative embodiments, the feeding fluid may comprise a variety of natural and/or artificial fluids/medium consistent with the objective of enabling the ticks to ingest the fluid/medium and harvesting usable biological products.

A "membrane" is defined as a thin, flexible, planar tissue structured so that a parasite can pierce a membrane and feed on a feeding fluid. A membrane is (at least) capable of being stretched across a vessel opening. In the preferred embodiment, the membrane comprises an animal skin (preferably a mouse/rat skin). More specifically, the membrane is selected based on the animal preferred by the particular tick species studied or otherwise utilized in a research/production operation. However the membrane may also comprise artificial/synthetic materials, as long as a parasite is capable of piercing the membrane and feeding on a feeding fluid.

Figure 2:
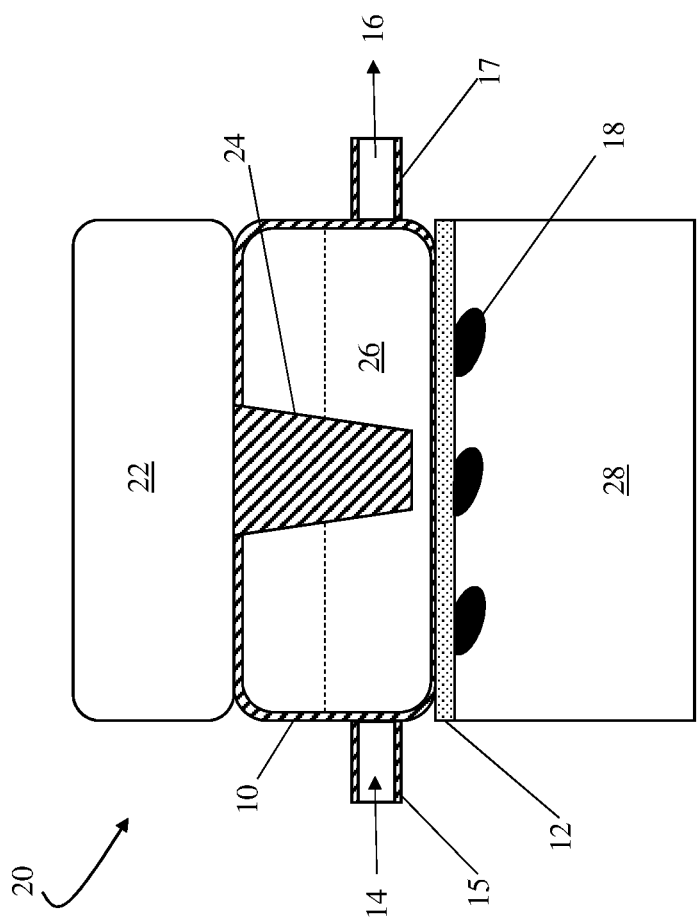
FIG. 2 is a partial sectional view of the tick feeding vessel (as shown along the section line II in FIG. 1) in combination with a fluid heater and a tick containment jar.

FIG. 2 shows the tick feeding vessel 10 in the context of other components of the tick feeding system 20. In addition to the feeding vessel 10, the system 20 further comprises a fluid heater 22 having a heating element 24 that extends downwardly into the animal blood 26. A tick containment jar 28 is shown as attached below the feeding vessel 10. Note that, in FIG. 2, although the feeding vessel 10 and the heating element 14 are shown in a sectional view (along the line II shown in FIG. 1), the fluid heater 22 and the tick containment jar 28 (which is preferably transparent) are not shown as sectional views.

With reference to FIG. 2 (as noted above with reference to FIG. 1), in basic embodiment, blood 26 is directed through an inlet port 15 in the direction of the arrow 14. After the blood 26 passes through the feeding vessel 10, it exits the feeding vessel 10 in the direction of the arrow 16 through the exit port 17.

In the preferred embodiment, the blood 26 in the feeding vessel 10 is maintained at the body temperature of the animal that the system 20 is seeking to replicate. In the preferred embodiment, the temperature is maintained by the heater 22. The heating element 24 may be an integral part of the heater 22. Alternatively, the heating element 24 may be an integral part of the upper portion of the feeding vessel 10—so that the heater 22 is separate from the heating element 24, but the heater 22 transfers heat to the heating element 24—and ultimately to the blood 26. In further alternative embodiments, the blood 26 may be preheated by any means known in the art before the blood enters the feeding vessel 10. In addition to heating the blood 26, the blood 26 may also be aerated or otherwise prepared before the blood 26 is circulated into the feeding vessel 10.

After the blood 26 leaves the feeding vessel 10, the blood 26 may be filtered to remove pathogens or other substance deposited in the blood 26 by the ticks 18. The blood 26 may be filtered or manipulated before and/or after the blood 26 leaves the vessel 10 by any means known in the art consistent with a researcher's or an operator's objectives.

The system 20 also comprises the tick containment jar 28. The jar 28 is important because at various stages of some species of tick's life cycle, the tick 18 drops off the host (i.e. simulated by the membrane 12). The jar 28 is necessary to contain the ticks 18 during this part of the growth cycle.

In operation, as shown in FIG. 1, an animal skin membrane 12 is attached to tick feeding vessel 10. As shown in FIG. 2, a tick containment vessel 28 is attached below the feeding vessel 10 and a fluid heater 22 is attached to the top of the feeding vessel 10. Ticks 18 attach themselves to the membrane 12 so that the ticks 18 feed on a feeding fluid (preferably blood) 26 through the membrane 12. The blood 26 is circulated through an inlet port 15 in the direction of the arrow 14. Once the blood 26 is in the feeding vessel 10, the blood 26 is warmed by the heating element 24 that is in communication with the heater 22. As the ticks 18 feed on the blood 26, the blood 26 is circulated out of the feeding vessel 10 in the direction of the arrow 16 through the outlet 17. After the blood 26 exits the feeding vessel 10, pathogens and other biological materials are removed from the blood 26 and the blood 26 is conditioned for recirculation.

For the foregoing reasons, it is clear that the in vitro tick feeding system described herein comprises a novel and innovative means of feeding ticks throughout the ticks' life cycle. The current system may be modified in multiple ways and applied in various technological applications. For example, the system described herein may also be used with leaches, fleas, parasitic worms, or other living things that feed on a host or by a similar means wherein that means could be replicated by this system.

The disclosed method and apparatus may be modified and customized as required by a specific operation or application, and the individual components may be modified and defined, as required, to achieve a desired result. Although the materials of construction are (mostly) not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

What is claimed is:

1. An in vitro parasite feeding system, the system comprising:
    a feeding vessel comprising a feeding fluid reservoir, the feeding fluid reservoir having an inlet, an outlet, and a membrane positioned across an opening in a bottom portion of the feeding fluid reservoir;
    wherein, during operation, feeding fluid is continuously circulated into the reservoir inlet, through the reservoir, and across a top surface of the membrane, and out the reservoir outlet, such that parasites on a bottom surface of the membrane simultaneously ingest the feeding fluid through the membrane.

2. The system of claim 1 wherein the system is structured so that the vessel is inverted and the feeding fluid is vertically supported by the membrane.

3. The system of claim 1 wherein the parasite comprises a tick.

4. The system of claim 1 wherein the parasite comprises one of a leach, flea, or parasitic worm.

5. The system of claim 1 wherein the feeding fluid comprises animal blood.

6. The system of claim 1 wherein the feeding fluid comprises a synthetic fluid.

7. The system of claim 1 wherein the membrane comprises an animal skin.

8. The system of claim 1 wherein the membrane comprises a mouse or rat skin.

9. The system of claim 1 wherein the membrane comprises a synthetic tissue.

10. The system of claim 1 wherein the feeding fluid is heated before it is circulated into the feeding vessel.

11. The system of claim 1 wherein the feeding fluid is heated while the fluid is in the feeding vessel.

12. The system of claim 11 wherein the feeding fluid is heated by an element extending vertically downwardly into the vessel.

13. The system of claim 1 wherein other substances may be added or removed from the feeding fluid before it enters the vessel.

14. A method of harvesting pathogens and biological products from parasites, the method comprising the steps of:
    (a) providing the system of claim 1;
    (b) after the feeding fluid is circulated out of the vessel, manipulating the feeding fluid to harvest pathogens and biological products.

15. The method of claim 14 further comprising:
    (c) reconditioning the feeding fluid;
    (d) circulating the feeding fluid back into the vessel.

16. The method of claim 15, wherein, in step (c), heating the feeding fluid to a target animal's body temperature.

17. A method of making and using an in vitro parasite feeding system, the method comprising the steps of:
    (a) providing a feeding fluid reservoir;
    (b) positioning a membrane across a bottom portion of an opening in the feeding fluid reservoir,
    (c) allowing parasites to attach to a bottom surface of the membrane;
    (d) feeding fluid is continuously circulated through the feeding fluid reservoir and over a top surface of the membrane, the parasites simultaneously feed on the feeding fluid through the bottom surface of the membrane.

18. The method of claim 17 wherein, in step (c), the parasites are ticks.

19. The method of claim 17 wherein, in step (d), the feeding fluid is blood.

\* \* \* \* \*